United States Patent [19]

Rheinheimer et al.

[11] Patent Number: 5,015,285
[45] Date of Patent: May 14, 1991

[54] AROMATIC CARBOXYLIC ACID DERIVATIVES AND THE USE THEREOF FOR CONTROLLING UNDESIRABLE PLANT GROWTH

[75] Inventors: Joachim Rheinheimer, Ludwigshafen; Peter Plath, Frankenthal; Karl Eicken, Wachenheim; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 409,408

[22] Filed: Sep. 19, 1989

[30] Foreign Application Priority Data

Sep. 22, 1988 [DE] Fed. Rep. of Germany ....... 3832237

[51] Int. Cl.$^5$ .................. A01N 43/54; C07D 239/34; C07D 239/38; C07D 239/28
[52] U.S. Cl. ........................................ 71/92; 544/299; 544/300; 544/301; 544/302; 544/310; 544/311; 544/312; 544/314; 544/316; 544/318; 544/319
[58] Field of Search ............... 544/299, 300, 301, 302, 544/310, 311, 312, 314, 316, 318, 319; 71/92

[56] References Cited

FOREIGN PATENT DOCUMENTS 0223406 5/1987 European Pat. Off. .
0249707 12/1987 European Pat. Off. .
0249708 12/1987 European Pat. Off. .

OTHER PUBLICATIONS

Remington's Pharmaceutical Sciences, 14th Ed., J. Hoover (Editor) Mack Pub. Co., Easton, PA. 1970, pp. 528-529.
Thornber, Isosterism and Molecular Modification in Drug Design; Chem. Soc. Reviews (1979) pp. 563-580.

Primary Examiner—Mary C. Lee
Assistant Examiner—J. Richter
Attorney, Agent, or Firm—Keil & Weinkauf

[57] ABSTRACT

Aromatic carboxylic acid derivatives of the formula

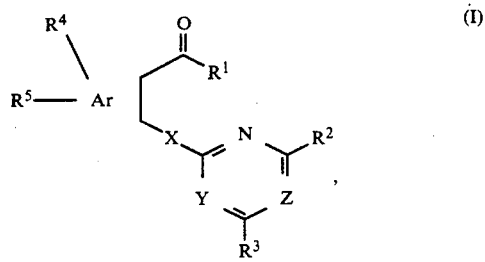

in which the radical

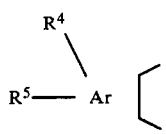

is a substituted or unsubstituted quinoline, naphthalene, benzofuran, thiophene or pyridine radical,
$R^1$ is hydrogen, alkylidenaminoxy, unsubstituted or substituted cycloalkylidenaminoxy, succinyliminoxy, unsubstituted or substituted alkenyloxy, alkynyloxy, azolyl, alkylsulfonylamino, alkoxycarbonylalkyloxy, N-azolylalkyloxy, unsubstituted or substituted alkoxy, unsubstituted or substituted phenylalkoxy, hydroxyl or the radical $O^\ominus M^\oplus$, $M^\oplus$ being one equivalent of an alkali metal, alkaline earth metal or organic ammonium ion,
$R^2$ and $R^3$ are alkyl, haloalkyl, alkoxy, haloalkoxy or alkylthio,
X is oxygen or sulfur,
Y and Z are nitrogen or the methine group, and
$R^4$ and $R^5$ are hydrogen, halogen, alkyl, haloalkyl, nitro, alkoxy, unsubstituted or substituted alkenyloxy, acylamino, alkylamino, dialkylamino or arylamino, and their use for controlling the growth of unwanted plants.

8 Claims, No Drawings

AROMATIC CARBOXYLIC ACID DERIVATIVES AND THE USE THEREOF FOR CONTROLLING UNDESIRABLE PLANT GROWTH

The present invention relates to novel aromatic carboxylic acid derivatives and the use thereof for controlling undesirable plant growth.

Herbicidal benzoic acid and pyridine carboxylic acid derivatives have been described in EP-A-223,406, EP-A-249,707 and EP-A-249,708.

We have found novel aromatic carboxylic acid derivatives of the formula

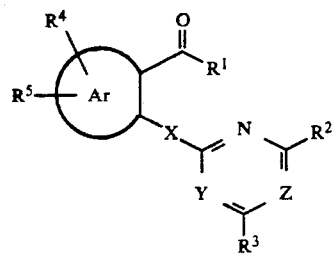

where the radical

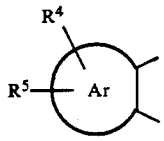

is a substituted or unsubstituted quinoline, naphthalene, benzofuran, thiophene or pyridine radical, $R^1$ is hydrogen, alkylideneaminoxy, unsubstituted or alenkyl-substituted cycloalkylideneaminoxy, succinyliminoxy, unsubstituted or alkyl- or halogen-substituted alkenyloxy, alkynyloxy, unsubstituted or chlorine- or methyl-substituted azolyl, alkylsulfonylamino, alkoxycarbonylalkyloxy, N-azolylalkyloxy, unsubstituted or alkylthio-, alkoxy-, cyano-, phenoxy-, alkylcarbonyl- or phenylcarbonyl-substituted alkoxy, unsubstituted or halogen-, methoxy- or methyl-substituted (in the phenyl) phenylalkoxy, hydroxyl or the radical $O^\ominus M^\oplus$, where $M^\oplus$ is one equivalent of an alkali metal, alkaline earth metal or organic ammonium ion, $R^2$ and $R^3$ are each alkyl, haloalkyl, alkoxy, haloalkoxy or alkylthio, X is oxygen or sulfur, Y and Z are each nitrogen or methine and $R^4$ and $R^5$ are each hydrogen, halogen, alkyl, haloalkyl, nitro, alkoxy, unsubstituted or alkyl- or halogen-substituted alkenyloxy, acylamino, alkylamino, dialkylamino or arylamino, with the proviso that X is sulfur when the radical

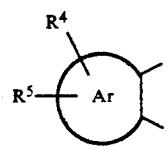

is a substituted or unsubstituted pyridine-2-carboxylic acid derivative, which are herbicidally active and selective toward crop plants, as are their agriculturally usable salts.

The present invention also covers those salts of the carboxylic acid derivatives which are less likely for use in agriculture but which can be important in the preparation of the carboxylic acids of the formula I.

In formula I, the substituents $R^1$, $R^2$, $R^3$, $R^4$ and $R^5$ have the following meanings:

$R^1$ is hydrogen, alkylideneaminoxy derived from the symmetrical or asymmetrical, branched or unbranched $C_3$-$C_{20}$-alkyl ketones, preferably from $C_3$-$C_{15}$-alkyl ketones, or from $C_8$-$C_{18}$-alkylphenyl ketones, preferably $C_8$-$C_{13}$-alkylphenyl ketones, unsubstituted or $C_1$-$C_4$-alkyl-, preferably methyl-, substituted $C_4$-$C_{12}$-, preferably $C_5$-$C_8$-, cycloalkylideneaminoxy, succinyliminoxy, $C_2$-$C_{10}$-, preferably $C_2$-$C_6$-, alkenyloxy or $C_2$-$C_{10}$-, preferably $C_2$-$C_6$-, alkynyloxy, which may each be substituted by $C_1$-$C_3$-alkyl or halogen, unsubstituted or chlorine- or methyl-substituted azolyl, such as imidazolyl, dichloroimidazolyl, pyrazolyl, dimethylpyrazolyl or triazolyl, $C_1$-$C_4$-alkylsulfonylamino, $C_3$-$C_{10}$-, preferably $C_3$-$C_7$-, alkoxycarbonylalkoxy, N-azolyl-$C_1$-$C_4$-alkoxy, unsubstituted or $C_1$-$C_3$-alkylthio-, $C_1$-$C_3$-alkoxy-, cyano-, phenoxy-, $C_1$-$C_3$-alkylcarbonyl- or phenylcarbonyl-substituted $C_1$-$C_{15}$-, preferably $C_1$-$C_{10}$-, alkoxy, unsubstituted or halogen-, methoxy- or methyl-substituted (in the phenyl) phenyl-$C_1$-$C_3$-alkoxy, hydroxyl or the radical $O^\ominus M^\oplus$, where $M^\oplus$ is one equivalent of an alkali metal, alkaline earth metal or an organic ammonium ion.

$R^2$ and $R^3$ may be identical or different and each is $C_1$-$C_5$-alkyl, $C_1$-$C_5$-haloalkyl, for example $C_1$-$C_3$-chloroalkyl or -fluoroalkyl, $C_1$-$C_5$-alkoxy, $C_1$-$C_5$-haloalkoxy, for example $C_1$-$C_2$-chloroalkoxy or -fluoroalkoxy, or $C_1$-$C_4$-alkylthio.

$R^4$ and $R^5$, which may be identical or different, are each for example hydrogen, halogen, nitro, $C_1$-$C_6$-alkyl, $C_1$-$C_6$-haloalkyl, for example $C_1$-$C_2$-chloroalkyl or -fluoroalkyl, $C_1$-$C_5$-alkoxy, $C_2$-$C_6$-alkenyloxy, which may be substituted by $C_1$-$C_3$-alkyl or halogen, $C_1$-$C_4$-monoalkylamino or -dialkylamino, acylamino, for example formylamino, acetylamino, pivaloylamino or benzoylamino, or arylamino, for example anilino.

Alkyl as alkyl and alkyl as alkoxy are each in accordance with the number of carbon atoms mentioned methyl, ethyl, propyl, isopropyl, butyl, sec.-butyl, tert.-butyl, pentyl and isomers, hexyl and isomers, heptyl and isomers or octyl and isomers. Similarly, the isomers are always included in the case of the higher homologs. Cycloalkylidene is for example cyclobutylidene, cyclopentylidene, cyclohexylidene, cycloheptylidene or cyclooctylidene. Alkenyl as alkenyl and alkenyl as alkenyloxy can each be vinyl, propenyl, butenyl, pentenyl, hexenyl or heptenyl. Aryl is preferably phenyl.

Of the above compounds or more specifically salts, in the case of acids, certain groups must be mentioned in particular, namely 1. those where $R^1$ is hydrogen, unsubstituted or $C_1$-$C_2$-alkylthio-, $C_1$-$C_3$-alkoxy-, cyano-, phenoxy-, $C_1$-$C_3$-alkylcarbonyl- or phenylcarbonyl-substituted $C_1$-$C_{10}$-alkoxy, unsubstituted or halogen-, methoxy-, or methyl-substituted (in the phenyl) $C_1$-$C_2$-phenylalkoxy, hydroxyl or the radical $O^\ominus M^\oplus$, where $M^\oplus$ is a sodium or potassium ion, alkylideneaminoxy derived from branched or unbranched $C_3$-$C_{11}$-alkyl ketones, $C_5$-$C_8$-cycloalkylideneaminoxy, propargyloxy, branched or unbranched $C_2$-$C_6$-alkenyloxy, $C_2$-$C_6$- chloroalkenyloxy, methylsulfonylamino, $C_1$–$C_3$-alkoxycarbonylmethoxy, imidazolyl, pyrazolyl or triazolyl, $R^2$ and $R^3$ are identical or different and each is $C_1$–$C_3$-alkyl, trifluoromethyl, trichloromethyl, $C_1$–$C_3$-alkoxy, difluoromethoxy or $C_1$–$C_3$-alkylthio, X is oxygen or sulfur, Y and Z are each nitrogen or methine, $R^4$ is hydrogen, fluorine, chlorine, bromine, $C_1$–$C_4$-alkyl, nitro, $C_1$–$C_4$-alkoxy, allyloxy, formylamino, acetylamino, pivaloylamino, benzoylamino, $C_1$–$C_3$-alkylamino or anilino, and $R^5$ is hydrogen, fluorine, chlorine, bromine or methyl, and where the radical

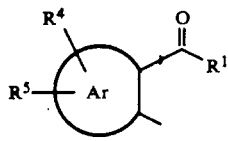

is derived from naphthalene-1-carboxylic acid, naphthalene-2-carboxylic acid, quinoline-2-carboxylic acid, quinoline-4-carboxylic acid, quinoline-8-carboxylic acid, thiophene-2-carboxylic acid or pyridine-4-carboxylic acid, or derivatives thereof, and 2. those where $R^1$ is hydrogen, unsubstituted or $C_1$–$C_2$-alkylthio-, $C_1$–$C_3$-alkoxy-, cyano-, phenoxy-, $C_1$–$C_3$-alkylcarbonyl- or phenylcarbonyl-substituted $C_1$–$C_{10}$-alkoxy, unsubstituted or halogen-, methoxy-, or methyl-substituted (in the phenyl) $C_1$–$C_2$-phenylalkoxy, hydroxyl or the radical $O^\ominus M^\oplus$, where $M^\oplus$ is a sodium or potassium ion, alkylideneaminoxy derived from branched or unbranched $C_3$–$C_{11}$-alkyl ketones, $C_5$–$C_8$-cycloalkylideneaminoxy, propargyloxy, branched or unbranched $C_2$–$C_6$-alkenyloxy, $C_2$–$C_6$-chloroalkenyloxy, methylsulfonylamino, $C_1$–$C_3$-alkoxycarbonylmethoxy, imidazolyl, pyrazolyl or triazolyl, $R^2$ and $R^3$ are identical or different and each is $C_1$–$C_3$-alkyl, trifluoromethyl, trichloromethyl, $C_1$–$C_3$-alkoxy, difluoromethoxy or $C_1$–$C_3$-alkylthio, X is sulfur, Y and Z are each nitrogen or methine, $R^4$ is hydrogen, fluorine, chlorine, bromine, $C_1$–$C_4$-alkyl, nitro, $C_1$–$C_4$-alkoxy, allyloxy, formylamino, acetylamino, pivaloylamino, benzoylamino, $C_1$–$C_3$-alkylamino or anilino, and $R^5$ is hydrogen, fluorine, chlorine, bromine or methyl, and where the radical

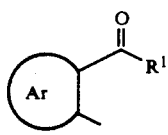

is pyridine-2-carboxylic acid or a derivative thereof.

Aromatic carboxylic acid derivatives of the formula I are obtained in a conventional manner by reacting an ortho-mercaptocarboxylic or ortho-hydroxy-carboxylic acid derivative of the formula II, which may either be known or preparable similarly to known compounds, with a heterocyclic compound of the formula III in the presence of a base.

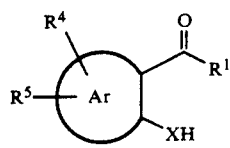

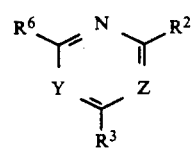

$R^6$ is a leaving group, such as chlorine, bromine, iodine, arylsulfonyl or alkylsulfonyl, for example toluenesulfonyl or methylsulfonyl.

The reaction temperatures are within the range from $-50°$ to $+160°$ C., preferably from 0° to 120° C. Suitable solvents are the usual solvents which are inert under the reaction conditions.

The compounds of the formula III which have a reactive substituent $R^6$ are in most cases known or easily preparable by any skilled worker without special training.

The base used can be from 1 to 10, preferably from 1 to 3, equivalents of alkali metal or alkaline earth metal hydrides such as NaH or $CaH_2$, alkali metal hydroxides such as NaOH or KOH, alkali metal alcoholates such as potassium tert.-butoxide, alkali metal carbonates such as $Na_2CO_3$ or $K_2CO_3$, alkali metal amides such as $NaNH_2$ or lithium diisopropylamide or tertiary amines. If an inorganic base is used, it is possible to add a phase transfer catalyst in order to increase the conversion.

Aromatic carboxylic acid derivatives of the formula I where $R^1$ is alkylideneaminoxy, unsubstituted or alkyl-substituted cycloalkylideneaminoxy, succinyliminoxy or unsubstituted or chlorine- or methyl-substituted azolyl and the other radicals have the same meanings as in the formula I defined in claim 1, can be prepared by first converting a carboxylic acid of the formula I where $R^1$ is hydroxyl into an activated form, for example a halide, mixed anhydride or imidazolide, in a conventional manner and then reacting this activated form with the corresponding hydroxyl compound. These are oximes, 1-hydroxysuccinylimine or azoles. In general it is necessary to carry out the reaction in the presence of a base. The two steps (activation and reaction) can be combined for example by preparing the activated form of the carboxylic acid in situ and reacting it further directly or by making the carboxylic acid act on the hydroxyl compound in the presence of a-water-eliminating agent such as, for example, a carbodiimide. This combined method is likewise encompassed by the invention.

Preparation Examples

EXAMPLE 1

Preparation of 2-(4,6-dimethoxypyrimidin-2-yloxy)-naphthalene-1-aldehyde 8.6 g (0.05 mol) of 2-hydroxynaphthalene-1-aldehyde are introduced into 50 ml of dry dimethylformamide and admixed by stirring, at 0°–5° C., with 1.5 g (0.05 mol) of 80% strength sodium hydride added a little at a time. 10.9 g (0.05 mol) of 4,6-dimethoxy-2-methylsulfonylpyrimidine are then added at room temperature, and the mixture is heated to 90° C. and stirred at that temperature for 6 hours. The solution thus obtained is poured into water. The aqueous mixture is extracted with methylene chloride, carefully washed with water, dried over sodium sulfate and concentrated under reduced pressure. The crude product is further purified by stirring out with cold toluene, leaving 7.4 g of 2-(4,6-dimethoxypyrimidin-2-yloxy)naphthalene-1-aldehyde of m.p. 123°–125° C.

EXAMPLE 2

Preparation of 2-(4,6-dimethoxypyrimidin-2-yloxy)-naphthalene-1-carboxylic acid 4.7 g (0.025 mol) of 2-hydroxynaphthalene-1-carboxylic acid are dissolved in 70 ml of methanol, and 1.6 g (0.025 mol) of potassium hydroxide (88% strength) are added. After 10 minutes, 200 ml of toluene are added, and the mixture is concentrated by heating under reduced pressure. After this procedure has been repeated once, the potassium salt thus obtained is dissolved in 120 ml of dry dimethyl sulfoxide, and 0.75 g (0.025 mol) of 80% strength sodium hydride are added at room temperature a little at a time. The mixture is subsequently stirred for 30 minutes and then admixed with 5.5 g (0.025 mol) of 4,6-dimethoxy-2-methylsulfonylpyrimidine. The mixture is subsequently stirred at room temperature for 2 hours and then poured into ice-water. The aqueous mixture is extracted twice with a little ethyl acetate; the extracts are discarded. The remainder is then strongly acidified with concentrated hydrochloric acid and extracted twice with ethyl acetate. The residue remaining after drying over sodium sulfate and concentrating is stirred up with a little diethyl ether. The product is filtered off and dried under reduced pressure, leaving 3.7 g of 2-(4,6-dimethoxypyrimidin-2-yloxy)naphthalene-1-carboxylic acid of m.p. 187°–189° C.

EXAMPLE 3

Preparation of methyl 3-(4,5-dimethoxypyrimidin-2-yloxy)thiophene-2-carboxylate 2.2 g (0.01 mol) of 4,6-dimethoxy-2-methylsulfonylpyrimidine and 1.6 g (0.01 mol) of methyl 3-hydroxythiophene-2-carboxylate are dissolved in 50 ml of ethyl methyl ketone, and 13.8 g (0.1 mol) of potassium carbonate are added. The mixture is refluxed for 4 hours, cooled down, diluted with water and extracted with methylene chloride. The extract is dried over sodium sulfate and concentrated under reduced pressure. The residue is stirred up with n-hephtane, filtered off and dried under reduced pressure, leaving 1.8 g of methyl 3-(4,5-dimethoxypyrimidin-2-yloxy)thiophene-2-carboxylate of m.p. 107°–109° C.

EXAMPLE 4

General method for preparing aromatic carboxylic acids of the formula I 0.073 mol of an aromatic 2-hydroxycarboxylic acid of the formula I is dissolved in 320 ml of dry dimethyl sulfoxide and admixed with 16.4 g (0.146 mol) of potassium tert.-butoxide added a little at a time, and the temperature of the reaction mixture rises to about 30° C. The reaction mixture is cooled to room temperature, 0.073 mol of a heterocyclic compound of the formula III is added, and the reaction mixture is subsequently stirred at room temperature for about 1 hour. (The end of the reaction can be checked by thin layer chromatography.) The reaction mixture is poured into about 2 l of cold water, acidified with hydrochloric acid and extracted with methyl tert.-butyl ether. The organic phase is washed with a little water, dried over sodium sulfate and concentrated. The remaining crude product can be purified, if necessary, by stirring up with a suitable solvent or by chromatography over silica gel.

EXAMPLE 5

General method for preparing aromatic carboxylic acids of the formula I 5.1 g of potassium hydroxide and 0.08 mol of a 2-hydroxycarboxylic acid of the formula II are dissolved in 80 ml of methanol, stirred at room temperature for 10 minutes and concentrated under reduced pressure. Thereafter, to dry the residue, toluene is repeatedly added and evaporated off at 50° C. under reduced pressure. The bright red powder thus obtained is taken up in 300 ml of dimethyl sulfoxide and admixed at room temperature with 2.9 g of 80% strength sodium hydride added a little at a time, and a gas evolves. Once the evolution of gas has ceased, a solution of 0.079 mol of a heterocyclic compound of the formula III in 80 ml of dimethyl sulfoxide is added dropwise, and stirred in for about 0.5 hours. The mixture is poured into 2 l of water, and the resulting mixture is neutralized with acetic acid and washed with methylene chloride. It is then strongly acidified with hydrochloric acid and repeatedly extracted with methyl tert.-butyl ether. The organic phase is dried over sodium sulfate, and the solvent is evaporated under reduced pressure. The substance remaining behind can be purified by chromatography over silica gel.

EXAMPLE 6

General method for preparing aromatic carboxylic acid derivatives of the formula I 3.2 mmol of a particular aromatic 2-(4,6-dimethoxypyrimidin-2-yloxy)carboxylic acid are presented in 20 ml of dimethoxyethane and admixed with 3.2 mmol of sodium hydride, and a gas begins to evolve at once. The reaction mixture is stirred at room temperature for 1 hour, cooled at 0° C. and admixed with 3.5 mmol of oxalyl chloride. It is subsequently stirred at 0° C. for 1 hour, and about 30% of the solvent is evaporated off under reduced pressure to remove the excess oxalyl chloride. 4.2 mmol of an oxime or of a corresponding hydroxy compound, dissolved in 10 ml of dimethoxyethane, are then added, followed by 3.2 mmol of pyridine at 0° C., and the mixture is warmed to room temperature in the course of 1 hour. The mixture is poured into 120 ml of cold water and extracted with methylene chloride. The organic phase is dried over sodium sulfate and concentrated under reduced pressure. The substance remaining behind can be further purified by chromatography over silica gel.

By these methods it is possible to prepare all the compounds of the formula I from the appropriate raw materials; if the tables below give physical data, these compounds of the formula I have been prepared. The other compounds listed are typical representatives of this class of substance.

The following compounds of the formula I can be obtained in a similar manner:

TABLE 1

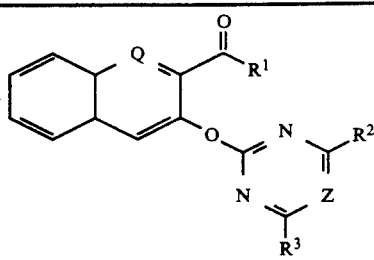

| No. | R¹ | Q | R² | R³ | Z | Phys. data* |
|---|---|---|---|---|---|---|
| 1.1 | OH | CH | OCH₃ | OCH₃ | CH | mp: 186–187° C. |
| 1.2 | OCH₃ | CH | OCH₃ | OCH₃ | CH | δ = 3.75 (3H); 3.80 (6H) 5.75 (1H); 8.55 (1H). |
| 1.3 | OCH₃ | CH | OCH₃ | OCH₃ | N | |
| 1.4 | OH | CH | OCH₃ | OCH₃ | N | |
| 1.5 | 2-propylidenaminoxy | CH | OCH₃ | OCH₃ | CH | |
| 1.6 | OH | CH | OCH₃ | CF₃ | CH | |
| 1.7 | OH | N | OCH₃ | OCH₃ | CH | mp: 135° C. (decomp.) |
| 1.8 | OCH₃ | N | OCH₃ | OCH₃ | CH | |
| 1.9 | H | N | OCH₃ | OCH₃ | CH | |
| 1.10 | OH | N | SCH₃ | SCH₃ | N | |

TABLE 2

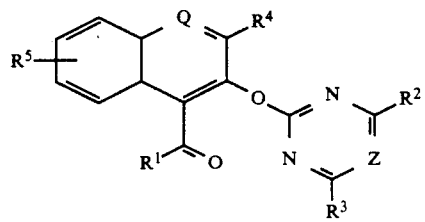

| No. | R¹ | Q | R² | R³ | R⁴ | R⁵ | Z | Phys. data* |
|---|---|---|---|---|---|---|---|---|
| 2.1 | OH | CH | OCH₃ | OCH₃ | H | H | CH | mp: 187–189° C. |
| 2.2 | OCH₃ | CH | OCH₃ | OCH₃ | H | H | CH | mp: 79–80° C. |
| 2.3 | 1-imidazolyl | CH | OCH₃ | OCH₃ | H | H | CH | |
| 2.4 | propargyloxy | CH | OCH₃ | OCH₃ | H | H | CH | mp: 122–124° C. |
| 2.5 | benzyloxy | CH | OCH₃ | OCH₃ | H | H | CH | |
| 2.6 | methylsulfonylamino | CH | OCH₃ | OCH₃ | H | H | CH | |
| 2.7 | 2-propylidenaminoxy | CH | OCH₃ | OCH₃ | H | H | CH | |
| 2.8 | H | CH | OCH₃ | OCH₃ | H | H | CH | mp: 123–125° C. |
| 2.9 | OH | N | OCH₃ | OCH₃ | H | H | CH | mp: 189–191° C. |
| 2.10 | OCH₃ | N | OCH₃ | OCH₃ | H | H | CH | mp: 103–105° C. |
| 2.11 | 2-propylidenaminoxy | N | OCH₃ | OCH₃ | H | H | CH | |
| 2.12 | OCH₃ | N | OCH₃ | OCH₃ | CH₃ | H | CH | mp: 142–144° C. |
| 2.13 | OH | CH | OCH₃ | OCH₃ | H | H | N | |
| 2.14 | OH | CH | SCH₃ | SCH₃ | H | H | N | |
| 2.15 | OCH₃ | CH | OCH₃ | SCH₃ | H | H | N | |
| 2.16 | OH | CH | CF₃ | OCH₃ | H | H | CH | |
| 2.17 | OH | CH | OCH₃ | OCH₃ | H | 6-NO₂ | CH | |
| 2.18 | OH | CH | OCH₃ | OCH₃ | H | 6-Br | CH | mp: 143–145° C. |
| 2.19 | O—CH₂SCH₃ | CH | OCH₃ | OCH₃ | H | H | CH | δ = 2.23 (s); 3.80 (s); 5.36 (s); 5.80 (s) |
| 2.20 | O—C₂H₄S—C₂H₅ | CH | OCH₃ | OCH₃ | H | H | CH | δ = 1.13 (t); 2.50 (q); 2.68 (t); 3.77 (s) 4.40 (t); 6.05 (s) |
| 2.21 | O—CH₂—C≡CH | CH | OCH₃ | OCH₃ | H | H | CH | mp: 122–124° C. |
| 2.22 | OC₂H₄—O—CH₃ | CH | OCH₃ | OCH₃ | H | H | CH | δ = 3.20 (3H); 3.50 (m,2H); 3.75 (s,6H); 4.40 (m,2H); 6.05 (s,1H) |

TABLE 3

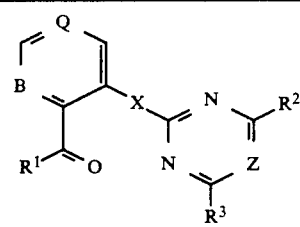

| No. | R¹ | B | Q | R² | R³ | X | Z | Phys. data* |
|---|---|---|---|---|---|---|---|---|
| 3.1 | OH | CH | N | OCH₃ | OCH₃ | O | CH | mp: 185–186° C. |
| 3.2 | OCH₃ | CH | N | OCH₃ | OCH₃ | O | CH | |
| 3.3 | benzyloxy | CH | N | OCH₃ | OCH₃ | O | CH | |
| 3.4 | 2-propylidenaminoxy | CH | N | OCH₃ | OCH₃ | O | CH | |
| 3.5 | OH | CH | N | CF₃ | OCH₃ | O | CH | |
| 3.6 | OH | CH | N | OCH₃ | OCH₃ | O | N | |
| 3.7 | OCH₃ | CH | N | SCH₃ | SCH₃ | O | N | |
| 3.8 | OH | N | CH | CH₃ | CH₃ | S | CH | |
| 3.9 | OCH₃ | N | CH | OCH₃ | OCH₃ | S | CH | |
| 3.10 | OH | CH | N | OCHF₂ | OCHF₂ | O | CH | |

TABLE 4

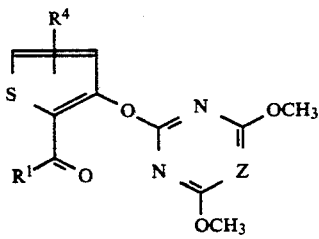

| No. | R¹ | R⁴ | Z | Phys. data* |
|-----|------|------|------|-------------|
| 4.1 | OCH₃ | H | CH | mp: 107–109° C. |
| 4.2 | OCH₃ | H | N | |
| 4.3 | allyloxy | H | CH | |
| 4.4 | OCH₃ | 5-Cl | CH | |
| 4.5 | OCH₃ | 4-CH₃ | CH | |

TABLE 5

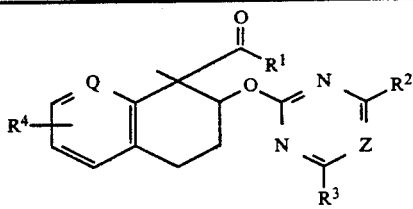

| No. | R¹ | Q | R² | R³ | R⁴ | Z | Phys. data |
|-----|------|---|------|------|-------|----|-------------|
| 5.1 | OCH₃ | N | OCH₃ | OCH₃ | 3-CH₃ | CH | mp: 131–132° C. |

*mp: melting point, $n_D$: refractive index, δ: $^1$H-NMR - chemic shift in ppm (selected signals).

The aromatic carboxylic acid derivatives of the formula I, or herbicidal agents containing them, have a herbicidal action and are selective in crop plants.

The compounds of the formula I, and herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1.1 is mixed with 10 parts by weight of N-methyl-alpha-pyrrolidone. A mixture is obtained which is suitable for application in the form of very fine drops.

II. 20 parts by weight of compound no. 1.1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.2 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 2.8 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 3.1 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 2.9 is intimately mixed with 97 parts by weight of particulate kaolin. A dust is obtained containing 3% by weight of the active ingredient.

VII. 30 parts by weight of compound no. 3.1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 2.1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or (preferably) postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5.0, preferably 0.01 to 0.5, kg of active ingredient per hectare.

Use examples

The herbicidal action of the carboxylic acid derivatives of the formula I on the growth of test plants is illustrated by the following greenhouse experiments.

The vessels employed were plastic flowerpots having a volume of 300 cm$^3$ and filled with a sandy loam containing about 3.0% humus. The seeds of the test plants were sown separately, according to species.

For the postemergence treatment, the plants were grown, depending on growth form, to a height of 3 to 15 cm before being treated. In this treatment method, either plants which had been sown in the pots and grown there were selected, or they were cultivated separately as seedlings and transplanted to the pots a few days before being treated with the compounds suspended or emulsified in water by spraying them through finely distributing nozzles. The application rate for postemergence treatment was 3.0 kg/ha.

The pots were set up in the greenhouse, species from warmer climates in warmer areas (20° to 35° C.) and species from moderate climates at 10° to 20° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the greenhouse experiments were Amaranthus retroflexus, Galium aparine and Triticum aestivum.

Active ingredients nos. 1.1, 1.2 and 2.1. applied postemergence at rates of 0.125 to 3.0 kg/ha, combated unwanted broadleaved plants excellently in cereals, without damaging the crop plants.

In view of the number of application methods possible, the compounds according to the invention, or agents containing them, may be used in a further large number of crops for removing unwanted plants. The following crops are given by way of example:

| Botanical name | Common Name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Phaseolus lunatus | limabeans |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |

-continued

| Botanical name | Common Name |
| --- | --- |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize | triazines, amides, ureas, diphenyl ethers, triazinones, uracils, benzo To increase the spectrum of action and to achieve synergistic effects, the carboxylic acid derivatives of the formula I may be mixed and applied together with numerous representatives of other herbicidal or growthregulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (het)aryloxyphenoxypropionic acids and salts, esters and amides thereof, etc.

It may also be useful to apply the compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. An aromatic carboxylic acid derivative of the formula I

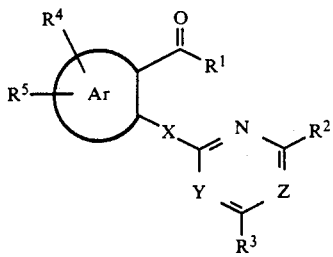

in which the radical

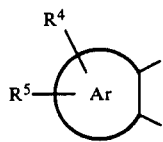

is a substituted or unsubstituted quinoline, naphthalene or benzofuran radical, $R^1$ is hydrogen, alkylidenaminoxy, unsubstituted or alkyl-substituted cycloalkylidenaminoxy, succinyliminoxy, unsubstituted or alkyl- or halogen-substituted alkenyloxy, alkynyloxy, unsubstituted or chloro- or methyl-substituted azolyl, alkylsulfonylamino, alkoxycarbonylalkyloxy, N-azolylalkyloxy, alkoxy which is unsubstituted or substituted by alkylthio, alkoxy, cyano, phenoxy, alkylcarbonyl or phenylcarbonyl, phenylalkoxy which is unsubstituted or substituted in the phenyl moiety by halogen, methoxy or methyl, hydroxyl or the radical $O^\ominus M^\oplus$, $M^\oplus$ being one equivalent of an alkali metal, alkaline earth metal or organic ammonium ion, $R^2$ and $R^3$ are alkyl, haloalkyl, alkoxy, haloalkoxy or alkylthio, X is oxygen or sulfur, one of Y or Z is nitrogen and the other is the methine group, and $R^4$ and $R^5$ are hydrogen, halogen, alkyl, haloalkyl, nitro, alkoxy, unsubstituted or alkyl- or halogen-substituted alkenyloxy, acylamino, alkylamino, dialkylamino or arylamino.

2. An aromatic carboxylic acid derivative of the formula I as set forth in claim 1, where the radical

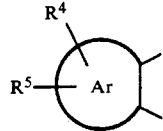

is substituted or unsubstituted quinoline or naphthalene.

3. A herbicidal composition containing inert carriers and a herbicidally effective amount of an aromatic carboxylic acid derivative of the formula I as set forth in claim 1.

4. A herbicidal composition containing inert carriers and a herbicidally effective amount of an aromatic carboxylic acid derivative of the formula I as set forth in claim 2.

5. A process for combating the growth of unwanted plants, wherein a herbicidally effective amount of a compound of the formula I as set forth in claim 1 is applied to the plants or their habitat.

6. A compound of the formula I as set forth in claim 1, wherein Y is N and Z is CH.

7. A process for conbating the growth of unwanted plants, wherein a herbicidally effective amount of a compound of the formula I as set forth in claim 6 is applied to the plants or their habitat.

8. A herbicidal composition containing inert carriers and a herbicidally effective amount of an aromatic carboxylic acid derivative of the formula I as set forth in claim 6.

* * * * *